United States Patent
Velasco Valcke

(10) Patent No.: US 11,448,667 B2
(45) Date of Patent: Sep. 20, 2022

(54) BIDIRECTIONAL SENSOR CIRCUIT

(71) Applicant: PANACEA QUANTUM LEAP TECHNOLOGY LLC, Dallas, TX (US)

(72) Inventor: Francisco Javier Velasco Valcke, Bogotá (CO)

(73) Assignee: PANACEA QUANTUM LEAP TECHNOLOGY LLC, Dallas, TX (US)

( * ) Notice: Subject to any disclaimer, the term of this patent is extended or adjusted under 35 U.S.C. 154(b) by 214 days.

(21) Appl. No.: 16/955,829

(22) PCT Filed: Dec. 21, 2018

(86) PCT No.: PCT/IB2018/060548
§ 371 (c)(1),
(2) Date: Jun. 19, 2020

(87) PCT Pub. No.: WO2019/123431
PCT Pub. Date: Jun. 27, 2019

(65) Prior Publication Data
US 2021/0072290 A1  Mar. 11, 2021

(30) Foreign Application Priority Data
Dec. 22, 2017  (CO) .................. NC2017/0013355

(51) Int. Cl.
*G01R 19/00* (2006.01)
*H03F 3/45* (2006.01)

(52) U.S. Cl.
CPC ..... *G01R 19/0023* (2013.01); *H03F 3/45475* (2013.01)

(58) Field of Classification Search
CPC ............ G01R 19/0023; H03F 3/45475; A61B 5/7225; A61B 5/30
See application file for complete search history.

(56) References Cited

U.S. PATENT DOCUMENTS

| | | | |
|---|---|---|---|
| 5,254,951 A | | 10/1993 | Goto et al. |
| 5,498,984 A | * | 3/1996 | Schaffer ................ H03F 3/3066 327/51 |

(Continued)

OTHER PUBLICATIONS

ELG4135L8, Apuntes Ramo. Universidad de Ottawa, [online] Jul. 12, 2017 [retrieved on Apr. 13, 2019], <https://web.archive.org/web/20170712154445/https://www.site/uottawa.ca/~rhabash/ELG4134L8.pdf>.

(Continued)

*Primary Examiner* — Dominic E Hawkins
(74) *Attorney, Agent, or Firm* — Faegre Drinker Biddle & Reath LLP

(57) ABSTRACT

A bidirectional sensor circuit includes a sensing impedance with first and second terminals; a first operational amplifier which non-inverting input is connected to the first terminal and its inverting input is connected to the second terminal; a second operational amplifier with the non-inverting input connected to the second terminal and its inverting input is connected to the first terminal; a first diode with the anode connected to the inverting input of the first operational amplifier and whose cathode is connected to the output of the first operational amplifier; and a second diode with the anode connected to the output of the first operational amplifier and to the cathode of the first diode. The input of the circuit consists of the terminals of the sensing impedance, and the output is at the anode of the second diode and senses a load impedance connected to the first terminal of the sensing impedance.

7 Claims, 12 Drawing Sheets

(56) References Cited

U.S. PATENT DOCUMENTS

| | | | |
|---|---|---|---|
| 6,985,774 B2 | 1/2006 | Kieval et al. | |
| 7,183,756 B1* | 2/2007 | Dikken | G01R 19/0092 |
| | | | 323/280 |
| 2012/0302821 A1 | 11/2012 | Burnett | |
| 2014/0254238 A1* | 9/2014 | Gilbert | G11C 13/004 |
| | | | 365/148 |
| 2019/0376854 A1* | 12/2019 | Quackenbush | G01L 5/161 |

OTHER PUBLICATIONS

OPA4330, Datasheet [en linea], Texas Instruments, 2016, [retrieved on Apr. 13, 2019], Retrieved from <http://www.ti.com/lit/ds/symlink/opa4330.pdf>.

INA193-INA198, Datasheet [en linea], Texas Instruments, 2015 [retrieved on Apr. 13, 2019], Retrieved from <http://www/ti.com/lit/ds/symlink/ina193.pdf>.

International Search Report dated Apr. 22, 2019 for PCT/IB2018/060548.

Written Opinion of the International Searching Authority dated Apr. 22, 2019 for PCT/IB2018/060548.

* cited by examiner

BIDIRECTIONAL SENSOR CIRCUIT

CROSS REFERENCE TO RELATED APPLICATIONS

This application is the National Stage of International Application No. PCT/IB2018/060548, filed Dec. 21, 2018, and claims benefit of Columbian Patent Application No. NC2017/0013355 filed on Dec. 22, 2017, both of which are incorporated herein in their entirety.

FIELD OF THE INVENTION

The current invention relates to bi-directional current sensors using operational amplifiers and ground reference decoupling circuits. The invention is related, in particular, to the use of precision rectifier circuits with operational amplifiers for the detection of changes in the current of an impedance.

BACKGROUND OF THE INVENTION

Many devices used to measure currents over an impedance connect the impedance to be measured to a measurement circuit, which is made up of coils or active devices, which in either way induce electrical noise to the impedance measurement, altering the precision of the measure.

For example, a Hall effect voltage sensor works well at low frequencies, but as the frequency increases, the inductor used causes an inductive reverse voltage that lowers the accuracy of the sensor, known as offset voltage and displacement temperature for which compensation is required, in the case of the present invention the sensor works independently from the magnetic force.

Efforts have also been made in the state of the art to build bidirectional sensors that are not connected to the impedance or to the conductor to be measured, for example, an ammeter clamp current sensor, which uses the same hall effect principle, and although it does not require direct contact with the electric current conductor, it is not sensible to currents below 400 A.

Moreover, other circuits used for sensing the current or voltage connect the impedance to be measured between the target ground and the reference ground, which becomes problematic when the electronic components change the ground reference and move with different values and current and voltage polarities.

In the state of the art, circuits are disclosed such as precision full-wave rectifiers which have the function to rectify a signal, in general alternating with an amplitude generally around the order of millivolts where the voltage drop in the diodes of the traditional rectifier circuit becomes an important variable. However, these circuits do not have an impedance connected between the positive and negative inputs of the operational amplifiers, which allows sensing of a load impedance of interest that is configured in such a way that the voltage output is proportional to the current on the impedance between the inverting and non-inverting input of the operational amplifiers.

In other inventions, such as U.S. Pat. No. 6,985,774B2, which shows a system that controls the cardiovascular reflex through the modulation or control of a baroreceptor activation device, which is a device that, among other techniques, electrically stimulates baroreceptors in the carotid sinus, the aortic arch, the heart, the common carotid arteries, the subclavian arteries and/or the brachiocephalic artery. It is evident that, in the biomedical field, electrically isolated devices are needed to measure or induce currents on tissues in living beings, so this type of sensors are necessary and can find their space in the market. Another example is document US2012/0302821 that shows a method and an apparatus for electromagnetically stimulating nerves, muscles, and body tissues where they use sensors that detect the stimulation generated by the circuit to the patient's body so that a control system is sometimes used to vary or modulate that current.

Also, among equipment for tissue stimulation employing electromagnetic fields, for example, and in study areas such as electromyography, sensors are used to record the body's electrical signals. It is well known that this equipment needs to limit the current that is directed towards the body of a patient, so the solution of several circuits is to place protection impedances limiting the current to the body, which means that they do not refer to the same ground level, so the sensing and measurement in these types of equipment at the output stage are difficult.

In summary, it is necessary to have a bidirectional sensing circuit that allows sensing to be carried out on circuits loads that do not have a reference to the same ground level, and for which correct operation at low frequencies is not affected.

BRIEF DESCRIPTION OF THE INVENTION

A bidirectional sensor circuit comprising: a sensing impedance with a first terminal and a second terminal; a first operational amplifier which non-inverting input is connected to the first terminal and its inverting input is connected to the second terminal; a second operational amplifier with the non-inverting input connected to the second terminal and its inverting input is connected to the first terminal; a first diode with the cathode connected to the inverting input of the first operational amplifier and which anode is connected to the output of the first operational amplifier; a second diode with the anode connected to the output of the first operational amplifier and to the cathode of the first diode; a variable impedance connected to the cathode of the first diode and the anode of the second diode; a fourth diode with the anode connected to the cathode of the second diode and to one end of the variable impedance; a third diode with the cathode connected to the inverting input of the second operational amplifier and the anode to the output of the second operational amplifier and to the cathode of the fourth diode; a variable impedance connected to the anode of the fourth diode and to the cathode of the third diode; wherein the input of the bidirectional sensor circuit consists of the terminals of the sensing impedance, and the output is at the anode of the second diode and senses a load impedance connected to the first terminal of the sensing impedance.

In this circuit the output is located at the anodes of the diodes by the output of both operational amplifiers that are shorted. The sensing impedance is small so that alterations on the impedance of the load to be measured are not included in the measurement.

The gains of the operational amplifiers could be adjusted by means of variable impedances and are adjusted in such a way that the output corresponds to the same exact value of the bidirectional current flowing at the load impedance.

The current invention should not be confused with a precision full-wave rectifier like the one shown in FIG. 1, unlike this rectifier, the current invention includes an impedance connected between the inverting and non-inverting inputs of the operational amplifiers, where the measurement is made. The gain of the amplifiers is adjustable, and it is configured in such a way that the voltage output is proportional to the current over the impedance between the negative and positive input of the operational amplifiers.

DETAILED DESCRIPTION OF THE INVENTION

A sensor is a device, module, or subsystem which purpose is to detect events or changes in the environment such as light, a force, vibrations, temperature, sound, a magnetic field, or electric current and sends information to other electronic components, usually a computer or processor. The sensing action is, for example, taking electrical changes in impedance and sending information in the form of modulated signals to another electronic component.

Figure 1:
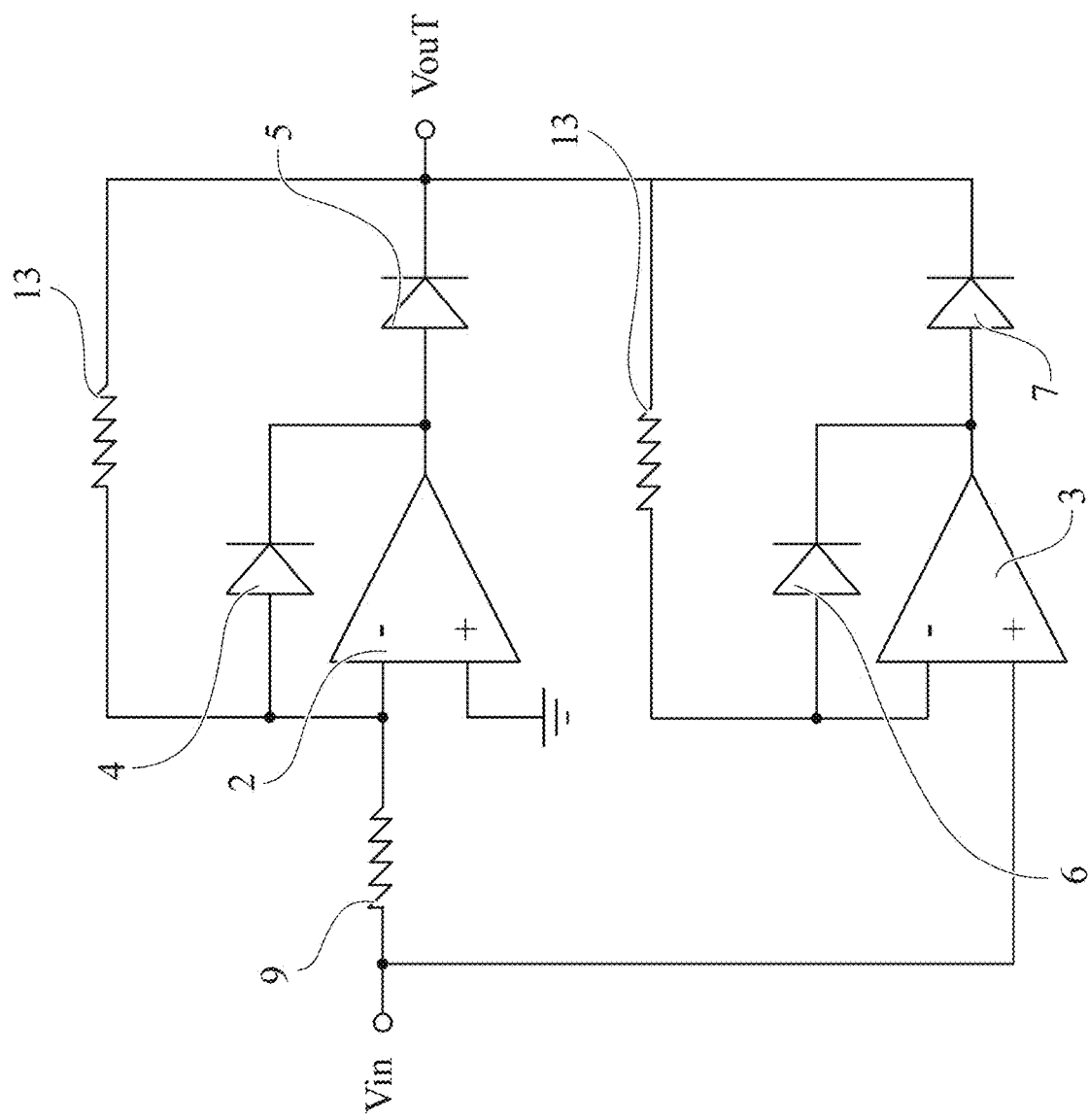
FIG. 1 shows a design of a known full-wave precision rectifier.
Figure 2:
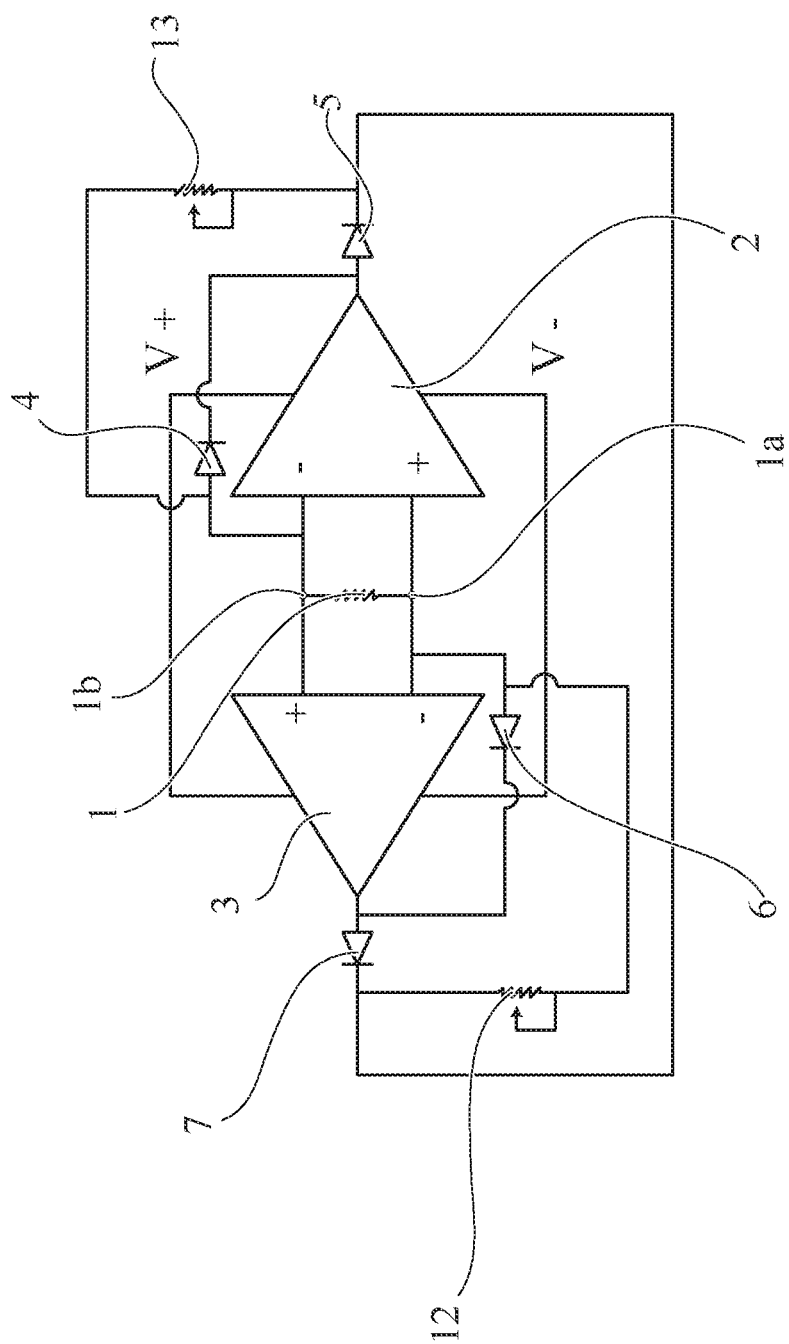
FIG. 2 shows a particular example of the current invention in a design with variable impedances for adjusting the gain; the inverting input of each of the operational amplifiers is connected to the non-inverting input of the other.

In FIG. 2, the current invention is a bidirectional sensor circuit consisting of: a sensing impedance (1) with a first terminal (1a) and a second terminal (1b); a first operational amplifier (2) which non-inverting input is connected to the first terminal (1a) and its inverting input is connected to the second terminal (1b); a second operational amplifier (3) with the non-inverting input connected to the second terminal (1b) and its inverting input is connected to the first terminal (1a); a first diode (4) with the anode connected to the inverting input of the first operational amplifier (2) and which cathode is connected to the output of the first operational amplifier (2); a second diode (5) with the anode connected to the output of the first operational amplifier (2) and to the cathode of the first diode (4); a variable impedance (13) connected to the anode of the first diode (4) and to the cathode of the second diode (5); a fourth diode (7) with the cathode connected to the cathode of the second diode (5) and to one end of the variable impedance (13); a third diode (6) with the anode connected to the inverting input of the second operational amplifier (3) and the cathode to the output of the second operational amplifier (3) and to the anode of the fourth diode (7); a variable impedance (12) connected to the cathode of the fourth diode (7) and to the anode of the third diode (6); where the input of the bidirectional sensor circuit consists of the terminals (1a) and (1b) the sensing impedance (1), and the output is at the anode of the second diode (5) and senses a load impedance connected to the first terminal (1a) of the sensing impedance (1).

The gain on the two operational amplifiers is adjusted so that the voltage output equals the same exact value of the current on the load impedance, and it is adjusted with the variable impedances (12) and (13) for a particular example of the invention they are variable impedances of any type.

As a particular example of the same invention, the circuit of a mesh between the sensing impedance (1) and the load impedance (14) the value of the current corresponds to an integer multiple of the voltage value at the first terminal (1a) of the sensing impedance (1).

Figure 3:
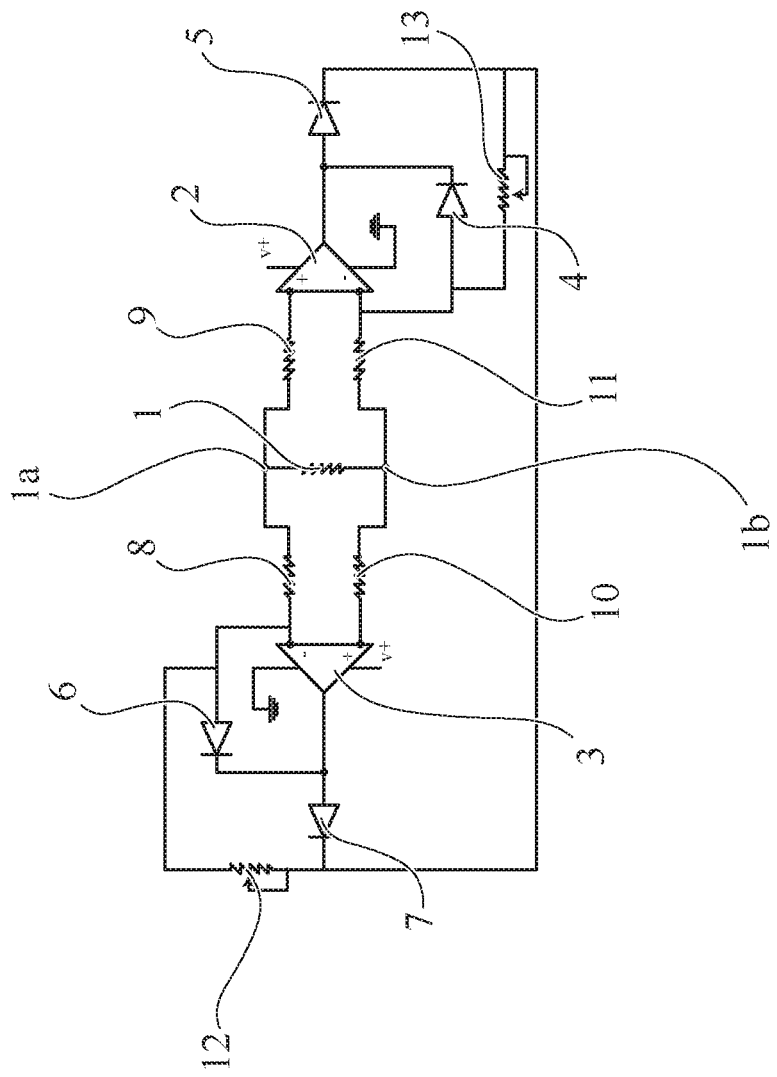
FIG. 3 shows a particular example of the current invention in a design with variable resistors to adjust the gain, and the inverting input of each of the operational amplifiers is connected to the non-inverting input of the other through impedances.

In FIG. 3, in another particular example of the invention, the bidirectional sensor circuit is characterized by the non-inverting input of the first operational amplifier (2) that is connected to the first terminal (1a) through an impedance (9) and its inverting input is connected to the second terminal (1b) through an impedance (11); the non-inverting input of the second operational amplifier (3) is connected to the second terminal (1b) through an impedance (10) and its inverting input is connected to the first terminal (1a) through an impedance (8); where operational amplifiers are powered with a positive voltage V+ and a negative voltage V−.

Figure 4:
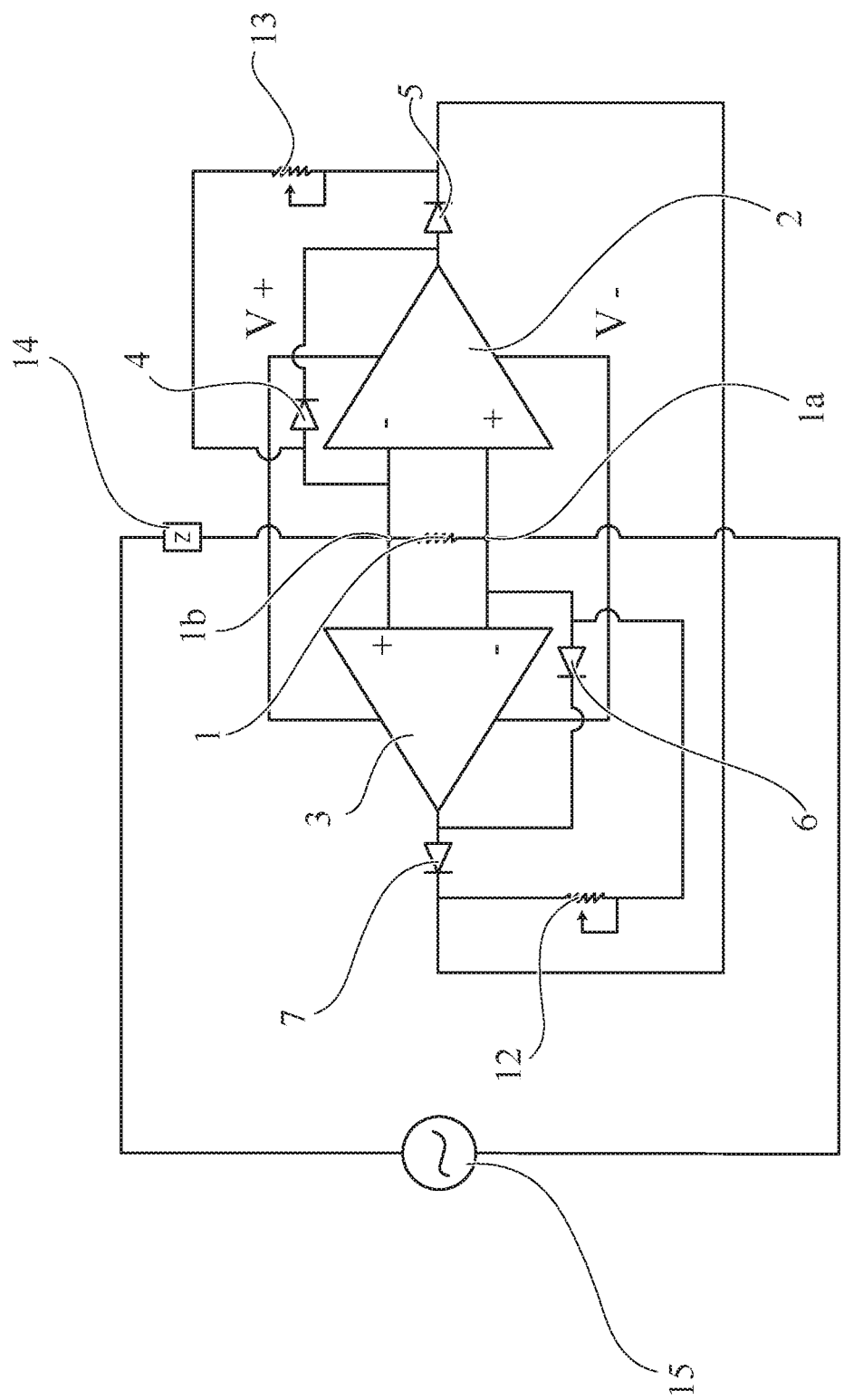
FIG. 4 shows a particular example of the current invention in a design with variable impedances to adjust the gain, and the inverting input of each of the operational amplifiers is connected to the non-inverting input of the other, an impedance-shaped circuit connected in series with an alternating current generator is connected in parallel to the sensing impedance.

In a new particular example of the invention, referring to FIG. 4, the bidirectional sensor circuit is connected to an alternating current source (15) in series with the load impedance (14), the other terminal of the load impedance (14) that is not connected to the alternating current source (15) connects to the first terminal (1a) of the sensing impedance (1), the free terminal of the alternating current source (15) connects to the second terminal (1b) of the sensing impedance (1), this allows laboratory tests to be carried out.

Figure 5:
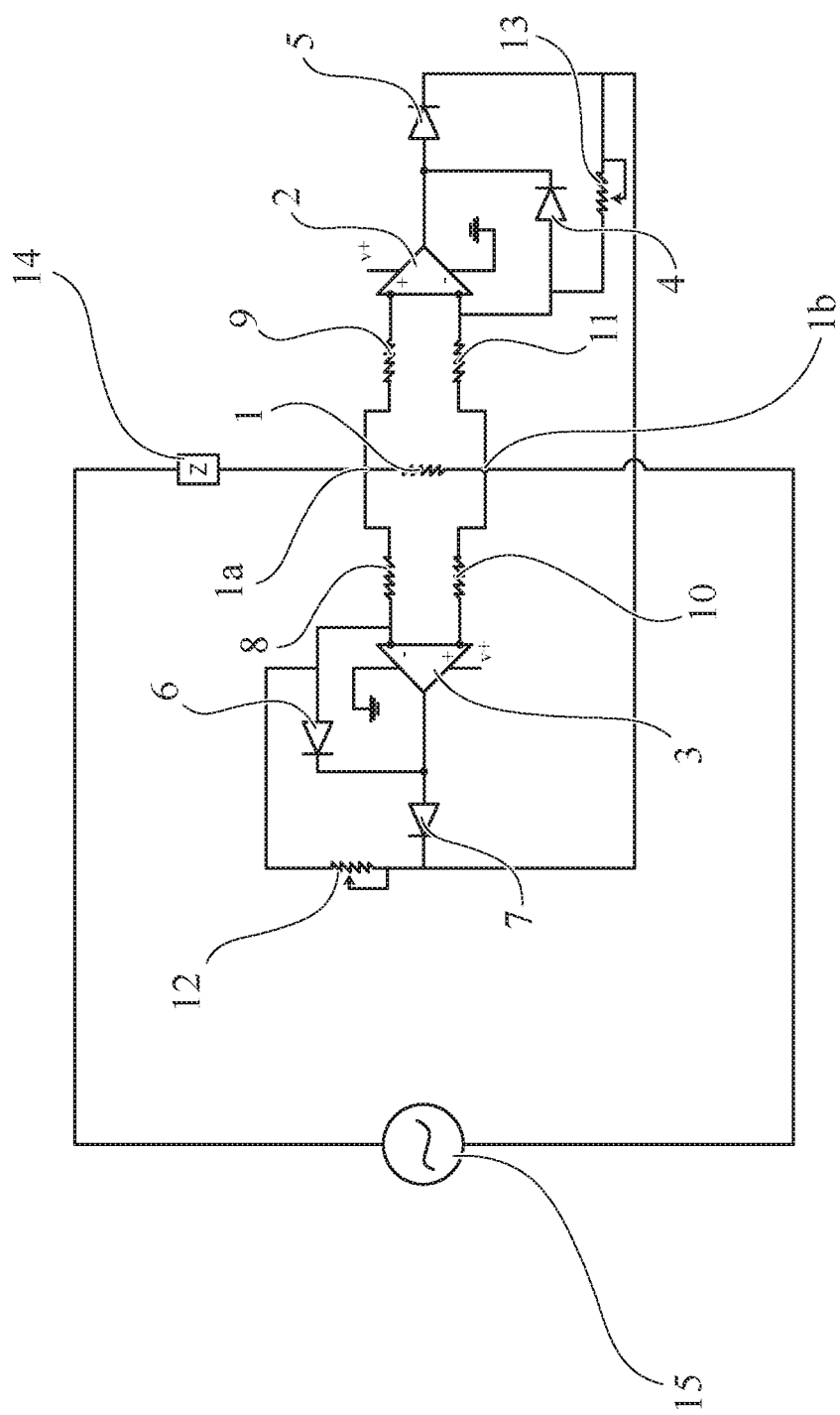
FIG. 5 shows a particular example of the current invention in a design with variable resistances to adjust the gain, and the inverting input of each of the operational amplifiers is connected to the non-inverting input of the other through impedances. Furthermore, a circuit includes an impedance connected in series to an alternating current generator connected in parallel to the sensing impedance.

In FIG. 5, the non-inverting input of the first operational amplifier (2) is connected to the first terminal (1a) through an impedance (9) and its inverting input is connected to the second terminal (1b) through an impedance (11); the non-inverting input of the second operational amplifier (3) is connected to the second terminal (1b) through an impedance (10) and its inverting input is connected to the first terminal (1a) through an impedance (8); and a positive voltage V+ and a negative voltage V− power the operational amplifiers. This is another particular example of the invention where the bidirectional sensor circuit is characterized by an alternating current source (15) connected in series with a load impedance (14) also connected to the first terminal (1a) with the second terminal (1b) connected to the free terminal of the alternating current source (15), to carry out laboratory tests.

Figure 6:
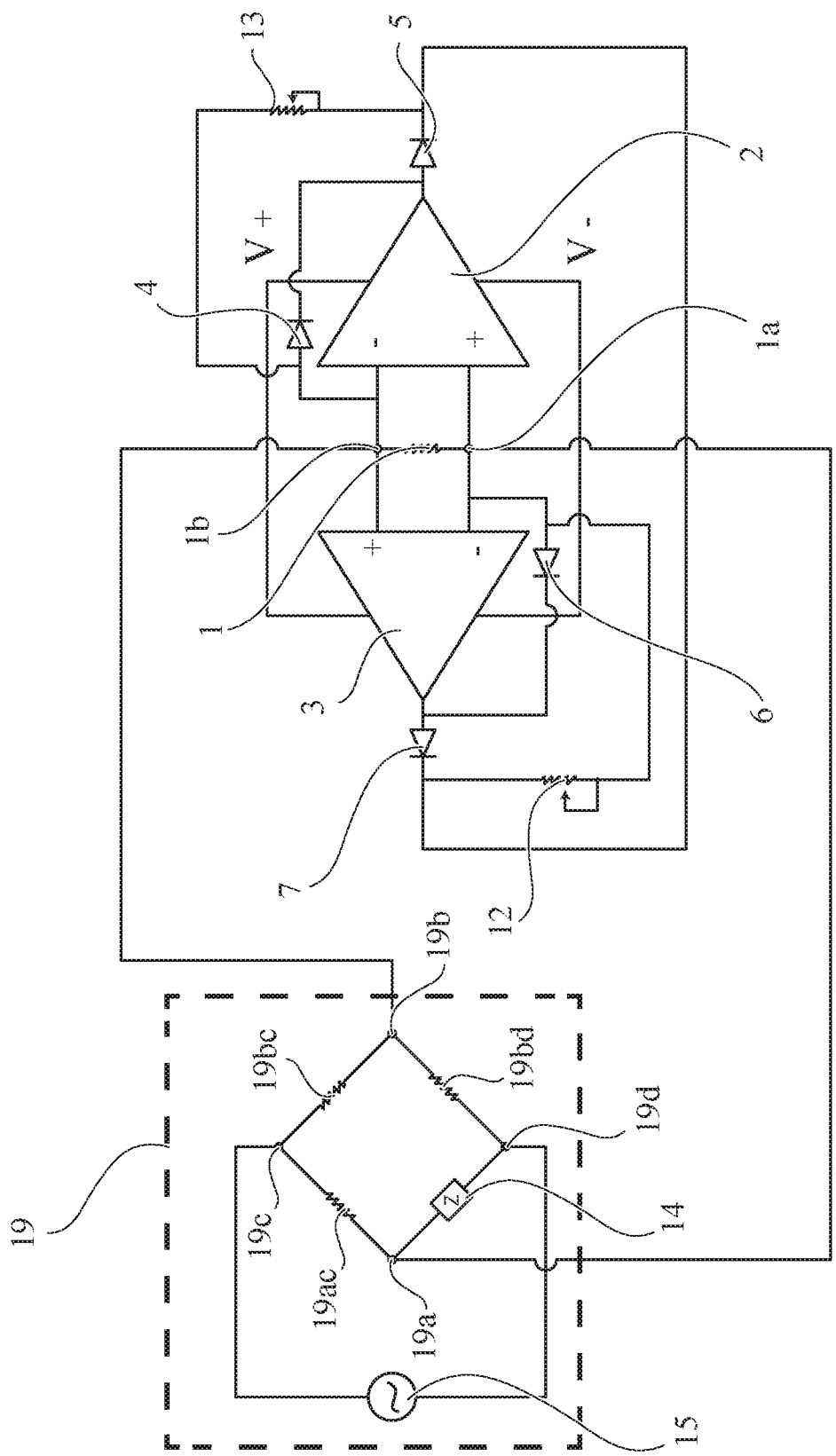
FIG. 6 shows a particular example of the current invention in a design with variable impedances to adjust the gain, and the inverting input of each of the operational amplifiers is connected to the non-inverting input of the other, in addition it is connected to a Wheatstone bridge.

FIG. 6 shows another particular example of the invention, where the terminals (1a) and (1b) of the sensing impedance (1) of the bidirectional sensor circuit are connected to an instrumentation Wheatstone bridge (19).

For the current invention, the instrumentation Wheatstone bridge (19) has: a first terminal (19a), a second terminal (19b), a third terminal (19c) and a fourth terminal (19d); a first impedance (19ac) connected to the first terminal (19a) and the third terminal (19c); a second impedance (19bc) connected to the second terminal (19b) and the third terminal (19c); a third impedance (19bd) connected to the second terminal (19b) and the fourth terminal (19d); an alternating current source (15) connected to the third terminal (19c) and the fourth terminal (19d); the first terminal (19a) connected to the second terminal (1b) of the sensing impedance (1); the second terminal (19b) connected to the first terminal (1a) of the sensing impedance (1); and a load impedance (14) is connected to the first terminal (19a) and the fourth terminal (19d).

Figure 7:
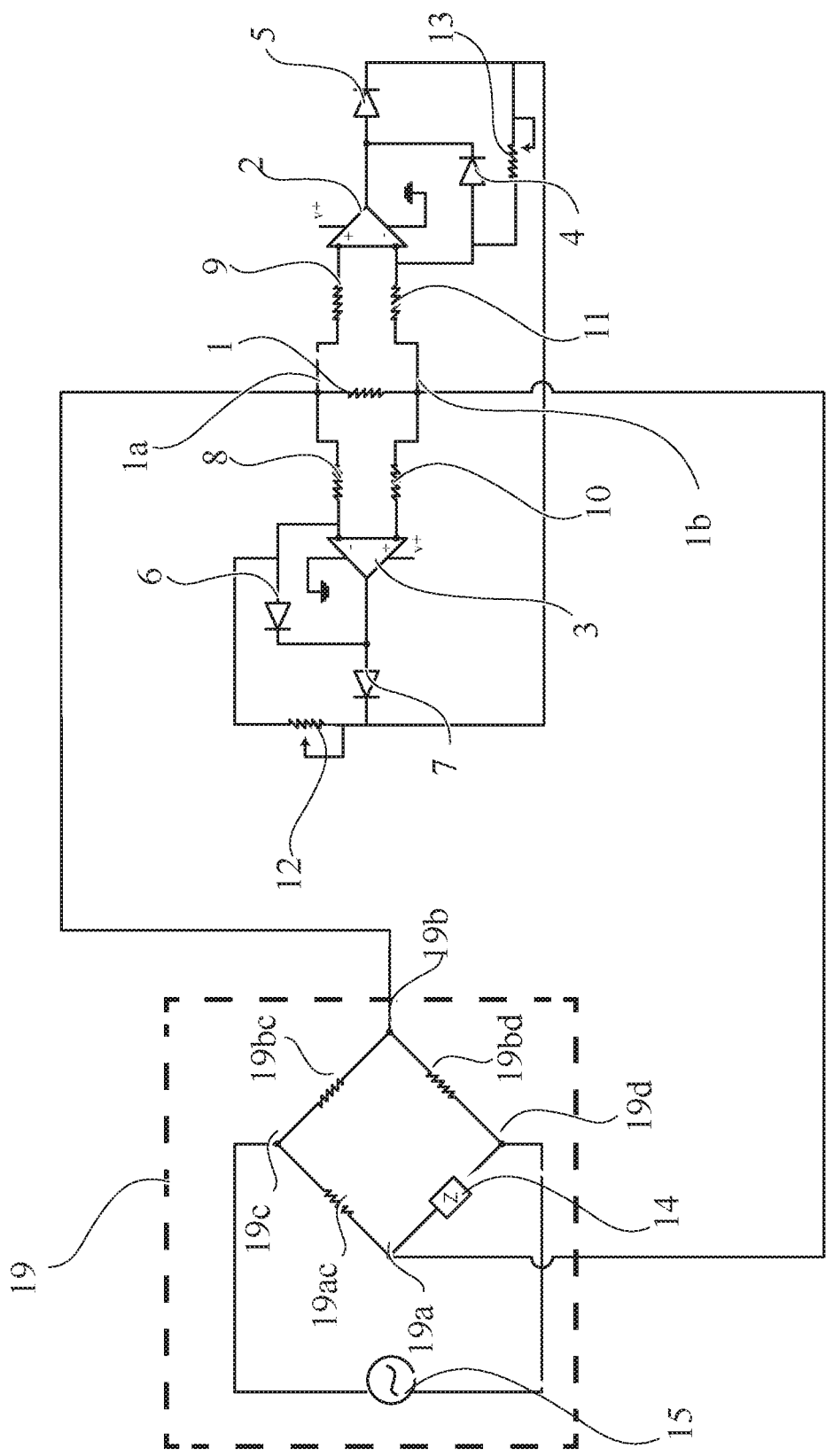
FIG. 7 shows a particular example of the current invention in a design with variable resistors to adjust the gain, and the inverting input of each of the operational amplifiers is connected to the non-inverting input of the other using impedances and also, it is connected to a Wheatstone bridge.

In FIG. 7, another particular example of the invention, for the bidirectional sensor circuit, the non-inverting input of the first operational amplifier (2) is connected to the first terminal (1a) through an impedance (9) and its inverting input is connected to the second terminal (1b) through an impedance (11); the non-inverting input of the second operational amplifier (3) is connected to the second terminal (1b) through an impedance (10) and its inverting input is connected to the first terminal (1a) through an impedance (8); and a positive voltage V+ and a negative voltage V− power the operational amplifiers. It also includes an instrumentation Wheatstone bridge (19) connected to terminals (1a) and (1b) of the sensing impedance (1).

For the current invention, the load impedance (14) corresponds to the impedance to be sensed in the circuit, in the case of a Wheatstone impedance bridge and for any particular example of the invention, this impedance is chosen from the group of variable impedances, photoresistors, thermoresistors, magnetic sensors, piezoelectric sensors, inductive sensors to measure a magnetic field, and electromagnetic transducers, among others, and combinations of the foregoing without being limited to this list.

Referring to the example in FIG. 5, in detail, during a positive half-cycle of an alternating current input signal on the sensing impedance (1) the alternating current input signal enters through the non-inverting input of the first operational amplifier (2), while the first diode (4) is open, the variable impedance (13) serves as the gain impedance, and the first operational amplifier (2) works in non-inverting amplifier mode, in this case the gain is calculated as is known by the value of the variable impedance (13) on the value of the impedance (11), the voltage over the impedance (1) is expanded and measured at the output of the diode (5). On the other hand, during the same positive half-cycle of the signal on the sensing impedance (1), the positive current on the diode (6) keeps it closed and the second operational amplifier (3) is configured in voltage follower mode. However, at the second terminal (1b) connected to the non-inverting input of the second operational amplifier (3), there is a negative voltage, which keeps the diode (7) open, so that at the output of the second operational amplifier (3) any voltage is perceived.

Meanwhile, during the negative half-cycle, the first operational amplifier (2) is configured in voltage follower mode, no voltage is perceived at the output of the diode (5) when receiving negative voltage on the first terminal (1a) connected to its non-inverting input makes the diode (5) open. The second amplifier (3) instead, has the diode (6) open so that the impedance (12) works as an amplification impedance, and then the second operational amplifier (3) is configured as a non-inverting amplifier with a positive voltage over its non-inverting input. Thus, this configuration maintains a positive voltage output.

The amplification gain on the operational amplifiers (2) and (3), is adjusted in such a way that the voltage output matches the same value of the current over the load impedance (14), preferably the value of the variable impedance (13) is variable just like the variable impedance value (12), and the impedance value of (11) and (8) is the same as well. The designer adjusts the gain of the circuit at will by varying the values of the variable impedances (13) and (12).

This configuration makes it possible for the outputs of both amplifiers to be interconnected as only one is conducting and, therefore, no voltage accidents occur. Furthermore, the sensing impedance (1) is, for example, at least one order of magnitude compared to the input impedance, so that the voltage measured over it is comparable to the voltage over the signal impedance at to measure.

Figure 8:
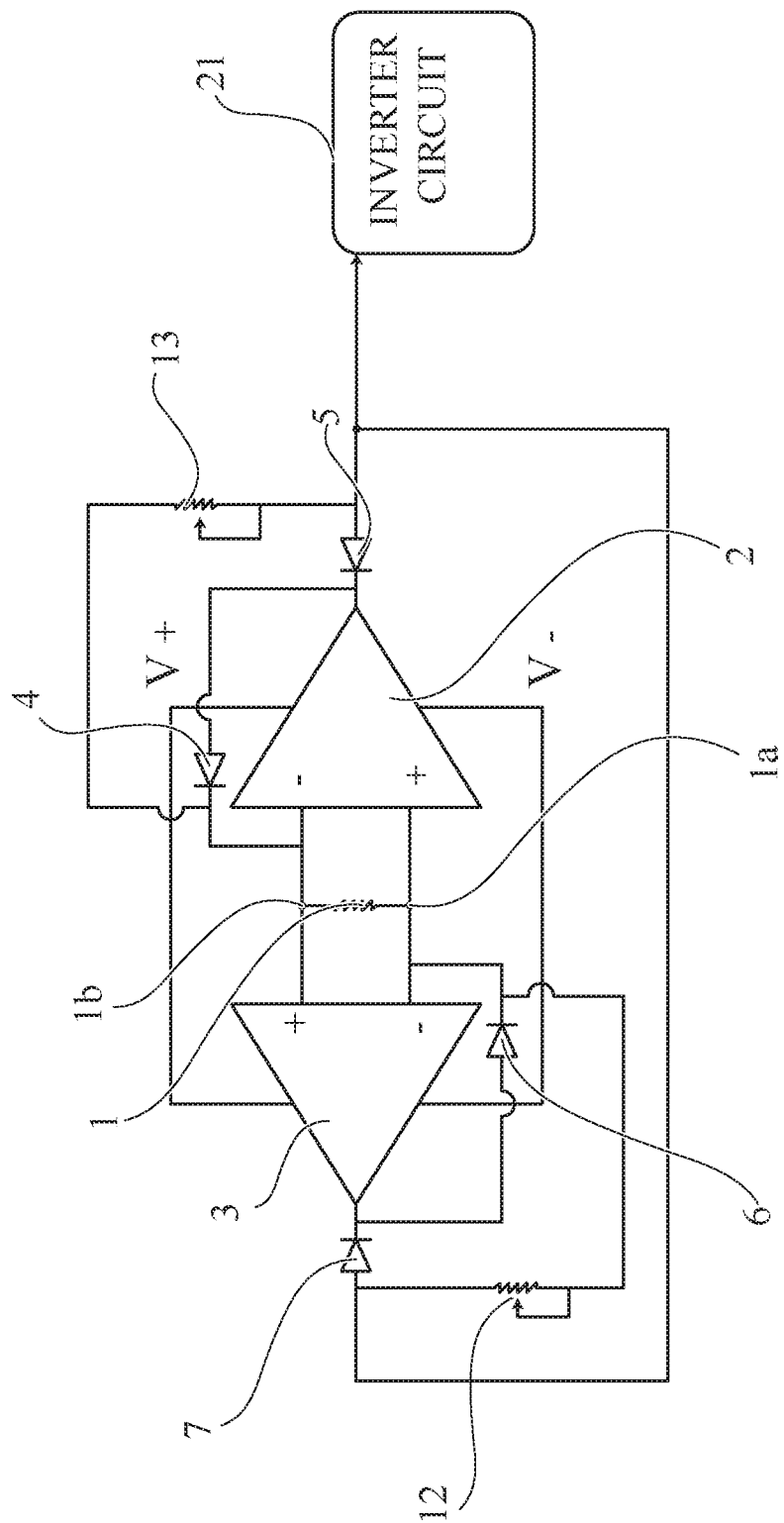
FIG. 8 shows a particular example of the current invention in a design with variable impedances to adjust the gain, and the inverting input of each of the operational amplifiers is connected to the non-inverting input of the other, with the diodes inverted and to an inverter at the output of the circuit.

In an alternative particular example of the invention, referring to FIG. 8, a reversed bidirectional sensor circuit, comprises: a sensing impedance (1) with a first terminal (1a) and a second terminal (1b); a first operational amplifier (2) for which the non-inverting input is connected to the first terminal (1a) and its inverting input is connected to the second terminal (1b); a second operational amplifier (3) with the non-inverting input connected to the second terminal (1b) and its inverting input is connected to the first terminal (1a); a first diode (4) with the cathode connected to the inverting input of the first operational amplifier (2) and for which the anode is connected to the output of the first operational amplifier (2); a second diode (5) with the cathode connected to the output of the first operational amplifier (2) and to the anode of the first diode (4); a variable impedance (13) connected to the cathode of the first diode (4) and to the anode of the second diode (5); a fourth diode (7) with the anode connected to the anode of the second diode (5) and to one end of the variable impedance (13); a third diode (6) with the cathode connected to the inverting input of the second operational amplifier (3) and the anode to the output of the second operational amplifier (3) and to the cathode of the fourth diode (7); a variable impedance (12) connected to the anode of the fourth diode (7) and to the cathode of the third diode (6); where the input of the bidirectional sensor circuit consists of the terminals (1a) and (1b) of the sensing impedance (1), and the output is at the anode of the second diode (5) connected to an operational inverter circuit (21), and senses a load impedance connected to the first terminal (1*a*) of the sensing impedance (1).

For the current invention, an operational inverter circuit is a circuit that inverts the input voltage and employs amplification, for example, an operational amplifier configured with unit negative gain or any gain as decided.

Figure 9:
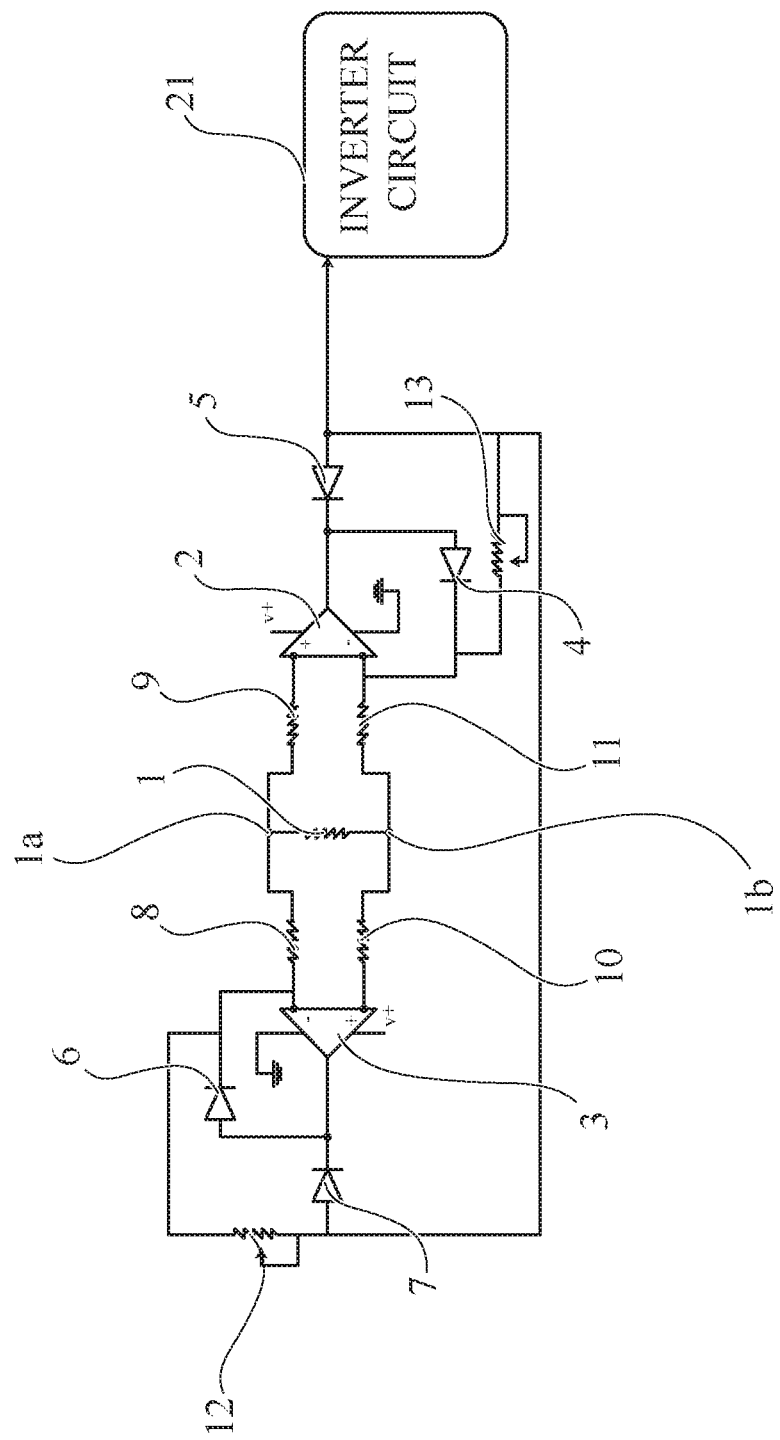
FIG. 9 shows a particular example of the current invention in a design with variable resistances to adjust the gain, and the inverting input of each of the operational amplifiers is connected to the non-inverting input of the other via impedances, with the diodes reversed and an inverter at the exit of the circuit.

In FIG. 9, as a particular example of the invention, for the reversing bidirectional sensor circuit the non-inverting input of the first operational amplifier (2) is connected to the first terminal (1*a*) through an impedance (9) and its inverting input connects to the second terminal (1*b*) through an impedance (11); the non-inverting input of the second operational amplifier (3) is connected to the second terminal (1*b*) through an impedance (10) and its inverting input is connected to the first terminal (1*a*) through an impedance (8); and a positive voltage V+ and a negative voltage V− power the operational amplifiers.

Figure 10:
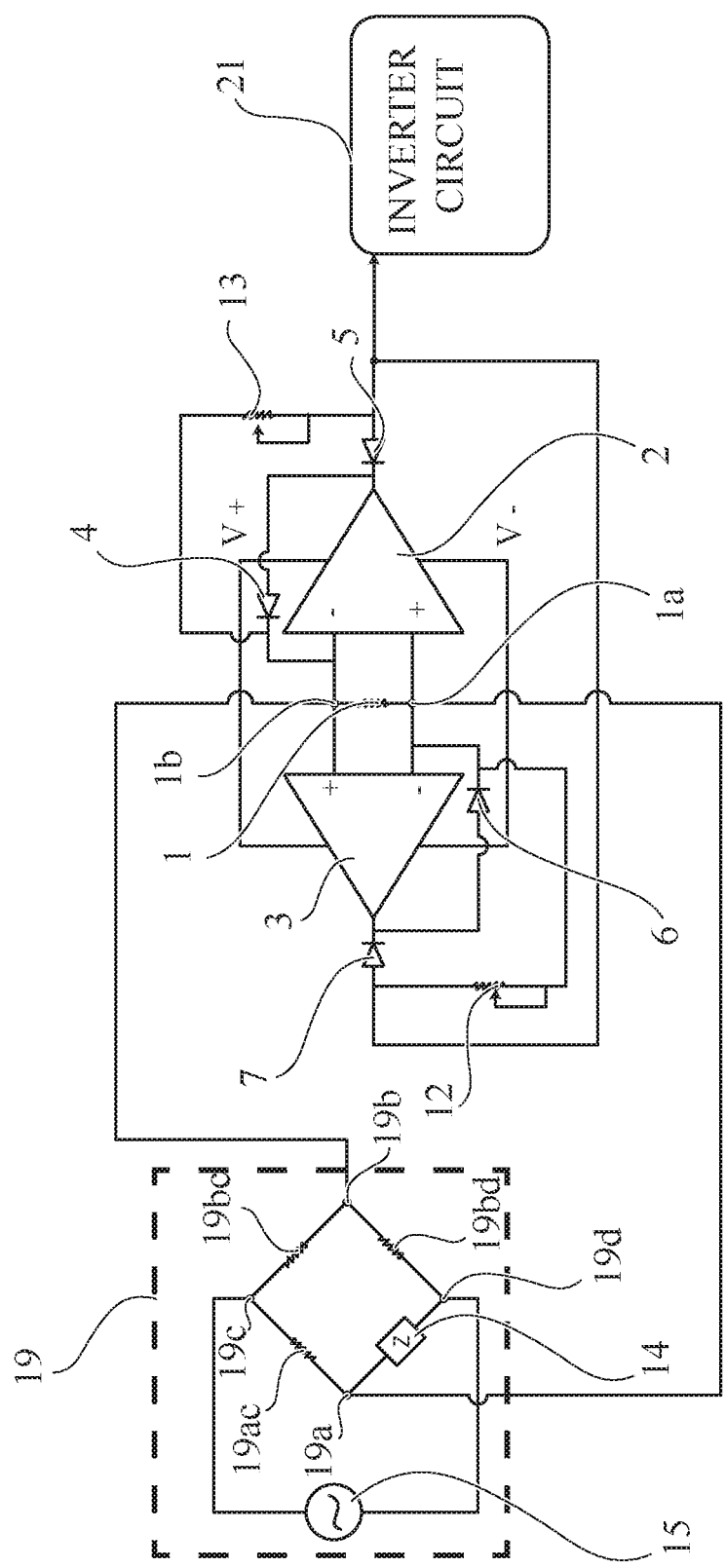
FIG. 10 shows a particular example of the current invention in a design with variable impedances to adjust the gain, and the inverting input of each of the operational amplifiers is connected to the non-inverting input of the other, with the diodes reversed, and it is also connected to a Wheatstone bridge and an inverter at the circuit output.
Figure 11:
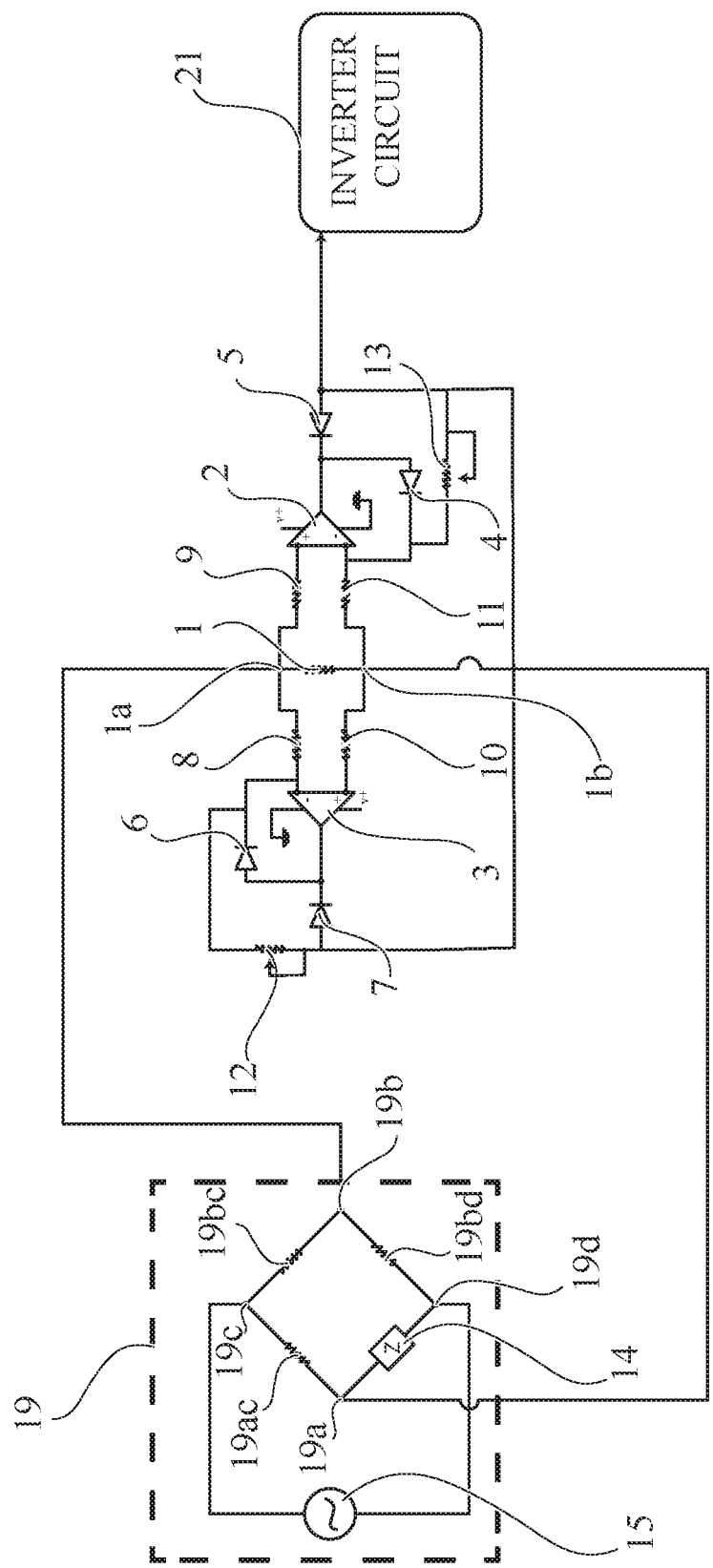
FIG. 11 shows a particular example of the current invention in a design with variable resistances to adjust the gain, and the inverting input of each of the operational amplifiers is connected to the non-inverting input of the other by means of impedances, with the diodes inverted, in addition it connects to a Wheatstone bridge and an inverter at the circuit output.

In FIG. 10, another example of the invention, the reversed bidirectional sensor circuit, shows an instrumentation Wheatstone bridge (19) connected to terminals (1*a*) and (1*b*) of the sensing impedance (1).

In FIG. 10, another particular example of the invention, the inverted bidirectional sensor circuit, where the non-inverting input of the first operational amplifier (2) is connected to the first terminal (1*a*) through an impedance (9) and its inverting input is connected to the second terminal (1*b*) through an impedance (11); the non-inverting input of the second operational amplifier (3) is connected to the second terminal (1*b*) through an impedance (10) and its inverting input is connected to the first terminal (1*a*) through an impedance (8); and a positive voltage V+ and a negative voltage V− power the operational amplifiers. It includes an instrumentation Wheatstone bridge (19) connected to terminals (1*a*) and (1*b*) of the sensing impedance (1).

Figure 12:
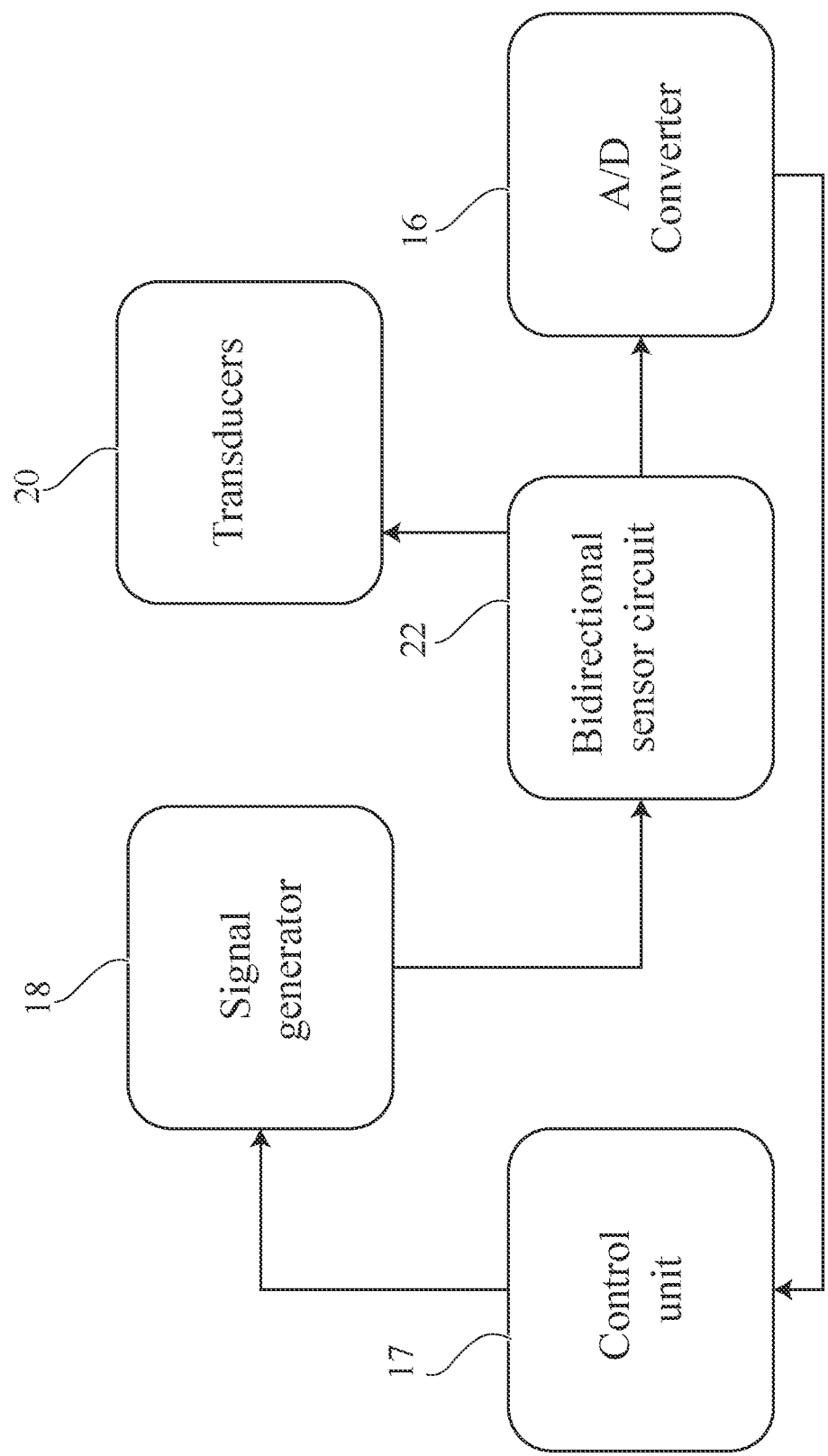
FIG. 12 shows is a block diagram of a specific example of the current invention.

In FIG. 12, as another example of the current invention, a circuit for sensing current changes on one or more transducers includes: a bidirectional sensor circuit (22); a digital analog converter (16) connected to the bidirectional sensor circuit (22); a control unit (17) connected to the digital analog converter (16); a signal generator (18) connected to the control unit (17); one or more transducers (20) connected to the output of the signal generator (18), and to the bidirectional sensor circuit (22); wherein the bidirectional sensor circuit (22) senses the current on the one or more transducers and sends a voltage that corresponds proportionally to the current on the one or more transducers (20).

It is possible to use the bidirectional sensor circuit to modulate a signal (for example, from a signal generator), in which the bidirectional sensor circuit is connected to sense the signal, and it is also connected to a digital-analog converter, and a control unit, allowing modulation and control of the signal generator.

Instead, as another particular example of the current invention, for the bidirectional sensor circuit the anode of the second diode (5) is connected to the input of a digital-analog converter (16); and a control unit (17) is connected to the output of the digital-analog converter (16).

In addition, the control unit (17) is connected to a signal generator (18) connected to a transducer (20), the transducer (20) is connected to the first terminal (1*a*) of the sensing impedance (1); wherein the transducer (20) is the load impedance (14).

The control unit (17) commands the signal generator (18) using feedback of the output signal of the digital-analog converter (16).

Likewise, as another example of the invention, the signal generator (18), is rather decoupled in impedance so as not to vary the load impedance (14).

It should be understood that the current invention is not limited to the examples described and illustrated as for an expert, there are variations and possible modifications that do not depart from the spirit of the invention, which is only defined by the following claims.

The invention claimed is:

1. A bi-directional sensor circuit comprising:
    a sensing impedance with a first terminal and a second terminal;
    a first operational amplifier for which the non-inverting input is connected to the first terminal and its inverting input is connected to the second terminal;
    a second operational amplifier with the non-inverting input connected to the second terminal and its inverting input is connected to the first terminal;
    a first diode with the anode connected to the inverting input of the first operational amplifier and for which the cathode is connected to the output of the first operational amplifier;
    a second diode with the anode connected to the output of the first operational amplifier and to the cathode of the first diode;
    a variable impedance connected to the anode of the first diode and to the cathode of the second diode;
    a fourth diode with the cathode connected to the cathode of the second diode and to one end of the variable impedance;
    a third diode with the anode connected to the inverting input of the second operational amplifier and the cathode to the output of the second operational amplifier and to the anode of the fourth diode;
    a variable impedance connected to the cathode of the fourth diode and the anode of the third diode;
    wherein the input of the bidirectional sensor circuit consists of the terminals and of the sensing impedance, and the output is at the anode of the second diode and senses a load impedance connected to the first terminal of the sensing impedance.

2. The circuit of claim 1, wherein the non-inverting input of the first operational amplifier is connected to the first terminal through an impedance and its inverting input is connected to the second terminal through an impedance; the non-inverting input of the second operational amplifier is connected to the second terminal through an impedance and its inverting input is connected to the first terminal through an impedance.

3. The circuit of claim 1, wherein the anode-cathode terminals of all the diodes are reversed, an inverter circuit is connected to the cathode of the diode, connected by its anode to the output of the first operational amplifier.

4. The circuit of claim 1, wherein the terminals and of the sensing impedance are connected to an instrumentation Wheatstone bridge; the instrumentation Wheatstone bridge has:
    a first terminal, a second terminal, a third terminal and a fourth terminal;
    a second impedance connected to the first terminal and to the third terminal;
    a third impedance connected to the second terminal and the third terminal;
    a fourth impedance connected to the second terminal and the fourth terminal;
    an alternating current generator connected to the third terminal and the fourth terminal;

the first terminal connected to the second terminal of the sensing impedance;

the second terminal connected to the first terminal of the sensing impedance; and a load impedance is connected to the first terminal and the fourth terminal.

5. The circuit of claim 1, wherein the anode of the second diode connects to the input of a digital-analog converter; and a control unit is connected to the output of the digital-analog converter.

6. The circuit of claim 5, wherein the control unit is connected to a signal generator connected to a transducer, the transducer is connected to the first terminal of the sensing impedance; wherein the transducer is the load impedance.

7. A bi-directional sensor circuit with inverter, comprising:

a sensing impedance with a first terminal and a second terminal;

a first operational amplifier for which the non-inverting input is connected to the first terminal and its inverting input is connected to the second terminal;

a second operational amplifier with the non-inverting input connected to the second terminal and its inverting input is connected to the first terminal;

a first diode with the cathode connected to the inverting input of the first operational amplifier and for which the anode is connected to the output of the first operational amplifier;

a second diode with the cathode connected to the output of the first operational amplifier and to the anode of the first diode;

a variable impedance connected to the cathode of the first diode and to the anode of the second diode; a fourth diode with the anode connected to the anode of the second diode and to one end of the variable impedance;

a third diode with the cathode connected to the inverting input of the second operational amplifier and the anode to the output of the second operational amplifier and to the cathode of the fourth diode;

a variable impedance connected to the anode of the fourth diode and the cathode of the third diode;

wherein the input of the bidirectional sensor circuit consists of the terminals and of the sensing impedance, and the output is at the anode of the second diode connected to an operational inverter circuit, and senses a load impedance connected to the first terminal of the sensing impedance.

\* \* \* \* \*